US007485855B2

(12) United States Patent
Sundaram et al.

(10) Patent No.: US 7,485,855 B2
(45) Date of Patent: Feb. 3, 2009

(54) ON-PROBE SAMPLE CLEANUP SYSTEM AND METHOD FOR MALDI ANALYSIS

(75) Inventors: Appavu K. Sundaram, Montgomery Village, MD (US); Nelli I. Taranenko, Columbia, MD (US); Vladimir M. Doroshenko, Ellicott City, MD (US)

(73) Assignee: Science and Engineering Services, Inc., Columbia, MD (US)

( * ) Notice: Subject to any disclaimer, the term of this patent is extended or adjusted under 35 U.S.C. 154(b) by 427 days.

(21) Appl. No.: 11/441,175

(22) Filed: May 26, 2006

(65) Prior Publication Data

US 2009/0001263 A1 Jan. 1, 2009

(51) Int. Cl.
*B01D 59/44* (2006.01)
*H01J 49/00* (2006.01)

(52) U.S. Cl. .................... 250/288; 250/281; 250/282; 424/421; 424/558; 436/178; 436/518; 436/525; 436/161; 436/287.9; 436/175; 977/891; 977/892; 977/881; 530/412; 530/419; 530/413; 435/4; 435/5; 435/6; 435/12; 435/7.1; 435/7.2; 435/7.23; 435/68.1; 435/272; 435/518; 435/320.1; 435/269; 506/5; 506/9; 506/12

(58) Field of Classification Search .................. 250/281, 250/282, 288; 424/421, 558; 436/178, 518, 436/525, 161, 287.9, 175; 977/891, 892, 977/881; 530/412, 419, 413; 435/4, 5, 6, 435/12, 7.1, 7.2, 7.23, 7.9, 68.1, 272, 518, 435/320.1, 269; 506/5, 9, 12
See application file for complete search history.

(56) References Cited

U.S. PATENT DOCUMENTS

| 6,555,813 | B1 * | 4/2003 | Beecher et al. ............. 250/281 |
| 2007/0275478 | A1 * | 11/2007 | Taranenko et al. .......... 436/175 |
| 2008/0193772 | A1 * | 8/2008 | Agroskin et al. ............ 428/421 |

OTHER PUBLICATIONS

James H. Strauss, Jr. et al., "Purification and Properties of Bacteriophage MS2 and of its Ribonucleic Acid", J. Mol. Biol., 7, 1963, pp. 43-54.
Doris E. Terry, et al., "Optimized Sample-Processing Time and Peptide Recovery for the Mass Spectrometric Analysis of Protein Digests", J. Am. Soc. Mass Spectrom., 15, 2004, pp. 784-794.
Hanjo Lim, et al., "Identification of 2D-Gel Proteins: A Comparison of MALDI/TOF Peptide Mass Mapping to μLC-ESI Tandem Mass Spectrometry", J. Am. Soc. Mass Spectrom., 14, 2003, pp. 957-970.

(Continued)

*Primary Examiner*—Jack I Berman
*Assistant Examiner*—Meenakshi S Sahu
(74) *Attorney, Agent, or Firm*—Oblon, Spivak, McClelland, Maier & Neustadt, P.C.

(57) ABSTRACT

A system and method for cleanup of biological samples from contaminants prior to spectroscopy analysis. The system includes a support configured to hold a sample including a liquid having at least one group of biological molecules with a surface of the support binding the molecules at a surface tension angle to the liquid of less than 180 degrees. The system includes an evaporator configured to evaporate liquid from the support, a solvent applicator configured to apply a solvent for dissolution of the contaminants in the sample, and a solvent removal device configured to remove applied solvent from the sample and thereby at least partially remove the contaminants.

40 Claims, 12 Drawing Sheets

OTHER PUBLICATIONS

Figure 1:
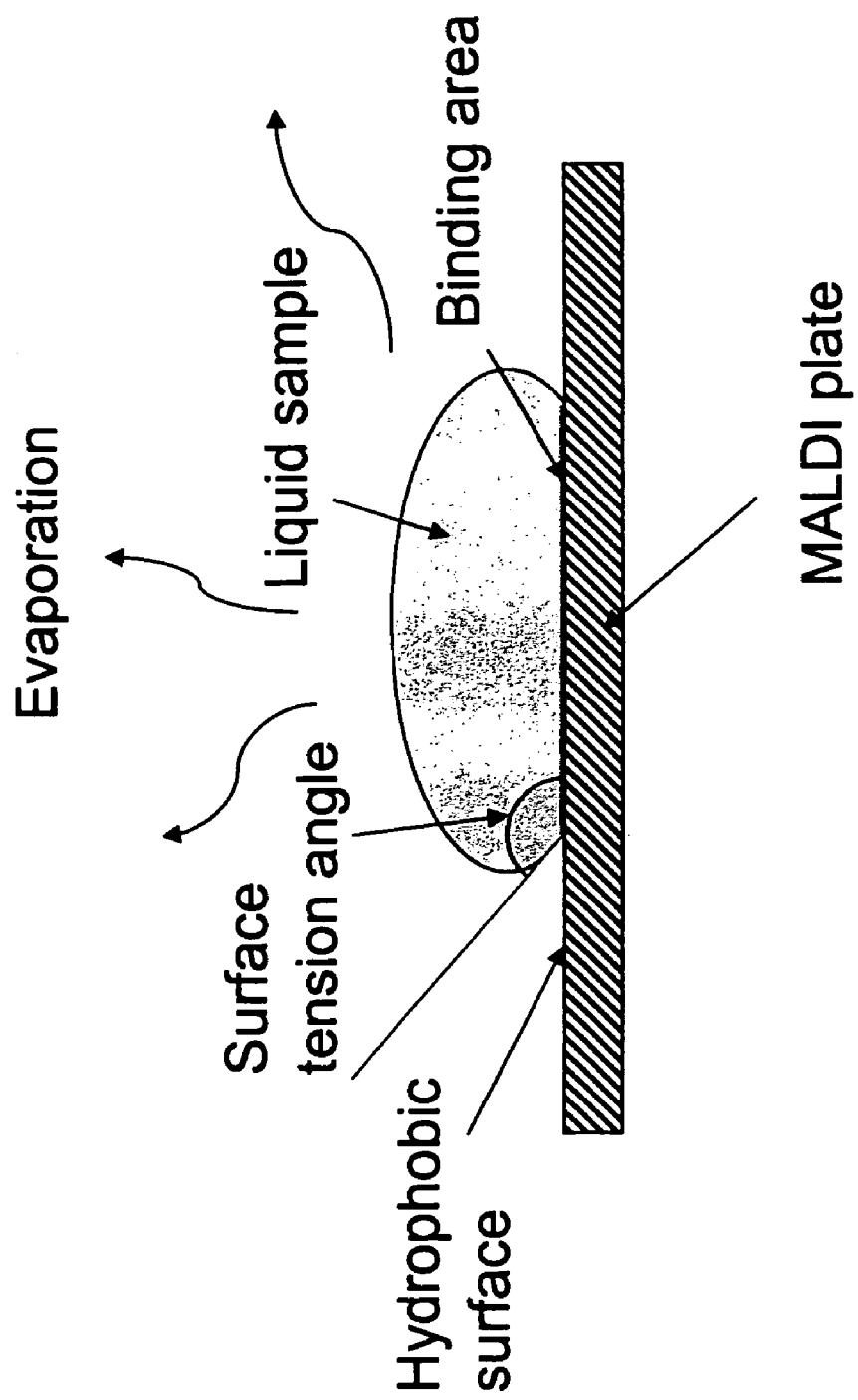
Figure 2:
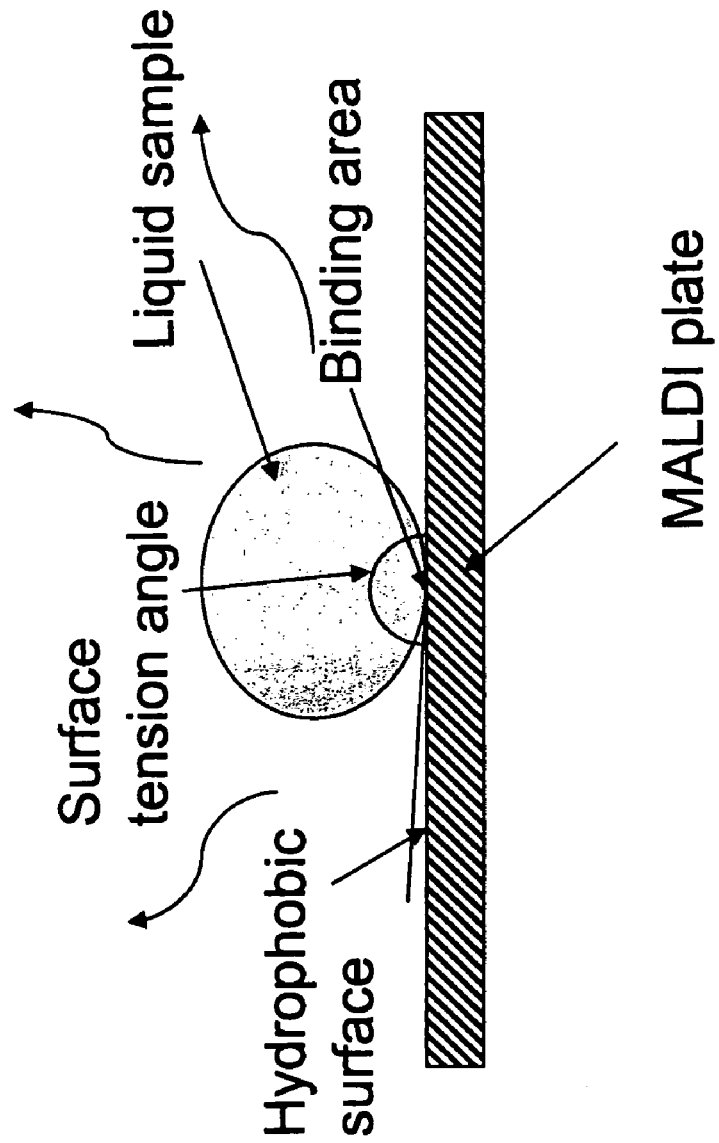

Jacob M. Hooker, et al., "Interior Surface Modification of Bacteriophage MS2", J. Am. Chem. Soc., vol. 126, No. 12, 2004, pp. 3718-3719.

Bryan M. Ham, et al., "MALDI-TOF MS of Phosphorylated Lipids in Biological Fluids Using Immobilized Metal Affinity Chromatography and a Solid Ionic Crystal Matrix", Analytical Chemistry, vol. 77, No. 14, Jul. 15, 2005, pp. 4439-4447.

Ronald C. Beavis, et al., "Rapid, Sensitive Analysis of Protein Mixtures by Mass Spectrometry", Proc. Natl. Acad. Sci. USA 87, vol. 87, Sep. 1990, pp. 6873-6877.

Maria Esteban Warren, et al., "On-Probe Solid-Phase Extraction/ MALDI-MS Using Ion-Pairing Interactions for the Cleanup of Peptides and Proteins", Analytical Chemistry, vol. 70, No. 18, Sep. 15, 1998, pp. 3757-3761.

Adam H. Brockman, et al., "Optimization of a Hydrophobic Solid-phase Extraction Interface for Matrix-Assisted Laser Desorption/ Ionization", Journal of Mass Spectrometry, 33, 1998, pp. 1141-1147.

Adam H. Brockman, et al., "Desalting Approach for MALDI-MS Using On-Probe Hydrophobic Self-Assembled Monolayers", Analytical Chemistry, vol. 69, No. 22, Nov. 15, 1997, pp. 4716-4720.

Michael Karas, et al., "Laser Desorption Ionization of Proteins with Molecular Masses Exceeding 10 000 Daltons", Analytical Chemistry, vol. 60, No. 20, Oct. 15, 1988, pp. 2299-2301.

\* cited by examiner

ON-PROBE SAMPLE CLEANUP SYSTEM AND METHOD FOR MALDI ANALYSIS

CROSS REFERENCE TO RELATED APPLICATIONS

This application is related to U.S. Ser. No. 11/441,176, filed May 26, 2006, entitled "Method and Apparatus for Processing of Biological Samples for Mass Spectrometry Analysis," the entire contents of which are incorporated herein by reference.

DISCUSSION OF THE BACKGROUND

1. Field of the Invention

The present invention relates to the field of analytical chemistry and mass spectrometry. This invention specifically relates to sample preparation and purification for analysis by mass spectrometry, particularly matrix-assisted laser desorption/ionization mass spectrometry (MALDI-MS).

2. Background of the Invention

MALDI is widely used for analyzing bio-molecules such as proteins, peptides, nucleic acids and lipids. However, MALDI is sensitive to the presence of interfering materials such as salts, buffers and chaotropes which result in signal suppression. Analysis of microorganisms by mass spectrometry using proteomics approaches has received attention recently due to the speed of analysis. In one approach, proteins from microbes are first extracted, digested using trypsin and purified before loading on to a MALDI target. Therefore, samples to be analyzed are usually cleaned and/or (partially) purified separately, before applying on to the MALDI probe surface. Currently, these cleaning and purification processes typically include chromatographic media and products such as C-18 ZipTips, C-8 ZipTips, and SPE columns. Biomolecules of interest are separated by selectively binding them to hydrophobic or hydrophilic groups attached to the chromatographic media.

Although these off-probe cleaning methods are generally good, there is often some sample loss in the chromatographic media, especially from samples containing low concentrations of analytes. Moreover, these clean up methods are time-consuming and require additional consumables and reagents that can be expensive.

Recently, self assembled monolayer surfaces have been developed as MALDI sample preparation platform and have demonstrated their usefulness in analyzing small volumes of peptides with high levels of contaminants. These techniques incubated the C-18 modified hydrophobic probes in the sample solution for more than 8 hours so as to effectively bind the analytes of interest. On probe cleaning methods by washing with deionized water prior to adding a MALDI matrix to the sample have been shown to significantly increase the protein sequence coverage. However, the long exposure of the probe surface to the sample solution to capture analyte biomolecules is one disadvantage of this method. In another approach, a small volume (1 μL) of the sample for analysis was dried on the probe surface (a procedure which took more than 10 minutes), and then was cleaned by washing the sample on the probe. Although this method appeared to work, the resultant spectra were fairly difficult to obtain since the analyte was localized to a very small region on the probe. As a result only few reasonable single-laser-shot spectra were obtained. This could be potentially explained by realizing that only a small amount of the peptide was bound to the hydrophobic surface due to a small contact area between a near-perfect sphere sample droplet and the hydrophobic surface, since a surface tension angle is close to 180 degrees. As a result the sensitivity of the method suffered due to a small number of analyte molecules binding to the probe surface.

The following articles related to sample preparation and analysis have been reported in the scientific literature, all of which are incorporated herein in entirety by reference:

1. Beavis, R. C. and B. T. Chait, *Rapid, sensitive analysis of protein mixtures by mass spectrometry*. Proc Natl Acad Sci USA, 1990. 87(17): p. 6873-7.
2. Karas, M. and F. Hillenkamp, *Laser desorption ionization of proteins with molecular masses exceeding 10,000 daltons*. Anal Chem, 1988. 60(20): p. 2299-301.
3. Ham, B. M., J. T. Jacob, and R. B. Cole, *MALDI-TOF MS of phosphorylated lipids in biological fluids using immobilized metal affinity chromatography and a solid ionic crystal matrix*. Anal Chem, 2005. 77(14): p. 4439-47.
4. Lim, H., et al., *Identification of 2D-gel proteins: a comparison of MALDI/TOF peptide mass mapping to mu LC-ESI tandem mass spectrometry*. J Am Soc Mass Spectrom, 2003. 14(9): p. 957-70.
5. Terry, D. E., E. Umstot, and D. M. Desiderio, *Optimized sample-processing time and peptide recovery for the mass spectrometric analysis of protein digests*. J Am Soc Mass Spectrom, 2004. 15(6): p. 784-94.
6. Brockman, A. H., B. S. Dodd, and R. Orlando, *A desalting approach for MALDI-MS using on-probe hydrophobic self-assembled monolayers*. Anal Chem, 1997. 69(22): p. 4716-20.
7. Brockman, A. H., N. N. Shah, and R. Orlando, *Optimization of a hydrophobic solid-phase extraction interface for matrix-assisted laser desorption/ionization*. J Mass Spectrom, 1998. 33(11): p. 1141-7.
8. Warren, M. E., A. H. Brockman, and R. Orlando, *On-probe solid-phase extraction/MALDI-MS using ion-pairing interactions for the cleanup of peptides and proteins*. Anal Chem, 1998. 70(18): p. 3757-61.
9. Hooker, J. M., E. W. Kovacs, and M. B. Francis, *Interior surface modification of bacteriophage MS2*. J Am Chem Soc, 2004. 126(12): p. 3718-9.
10. Strauss, J. H., Jr. and R. L. Sinsheimer, *Purification and properties of bacteriophage MS2 and of its ribonucleic acid*. J Mol Biol, 1963. 7: p. 43-54.

Despite this work, suitable sample preparation techniques are still needed.

SUMMARY OF THE INVENTION

Accordingly, one object of the present invention accomplished in various of the embodiments is to provide a system (and corresponding method) for cleanup of biological samples from contaminants prior to spectroscopy analysis.

Another object of the present invention accomplished in various of the embodiments is to provide a system (and corresponding method) to bind the biomolecules to the hydrophobic surface of the support while drying the sample.

Another object of the present invention accomplished in various of the embodiments is to provide a system (and corresponding method) for improving the surface tension between a liquid sample and a hydrophobic support holding the liquid sample for spectroscopy analysis.

Yet another object of the present invention accomplished in various of the embodiments is to provide a system (and corresponding method) for removal of contaminants from a liquid sample prior to spectroscopy analysis.

Various of these and other objects are provided for in certain ones of the embodiments of the present invention.

In one embodiment of the present invention, there is provided a system for cleanup of biological samples from contaminants prior to spectroscopy analysis. The system includes a support configured to hold a sample including a liquid having at least one group of biological molecules with a surface of the support binding the molecules. The system includes a reagent applicator configured to apply a reagent/wetting agent to reduce the surface tension angle between the liquid and the surface of the support to less than 180 degrees. The system includes an evaporator configured to evaporate liquid from the support, a solvent applicator configured to apply to the support a solvent for dissolution of the contaminants in the sample, and a solvent removal device configured to remove the applied solvent from the sample and thereby remove at least a part of the contaminants.

In one embodiment of the present invention, there is provided a method for cleanup of biological samples from contaminants prior to spectroscopy analysis. The method deposits on a support a sample including a liquid having at least one group of biological molecules, and adds a reagent to the sample so as to reduce the surface tension angle of the liquid to the support to less than 180 degrees while the sample dries out. The method dries the sample by evaporation, and applies a solvent for dissolution of the contaminants in the sample, and removes the applied solvent from the sample thereby remove at least a part of the contaminants.

It is to be understood that both the foregoing general description of the invention and the following detailed description are exemplary, but are not restrictive of the invention.

BRIEF DESCRIPTION OF THE DRAWINGS

A more complete appreciation of the present invention and many attendant advantages thereof will be readily obtained as the same becomes better understood by reference to the following detailed description when considered in connection with the accompanying drawings, wherein:

FIG. 1 is a schematic illustration according to one embodiment of the present invention showing an increased area during sample drying for binding sample biomolecules to a hydrophobic surface;

FIG. 2 is a schematic illustration of a conventional technique showing that the binding area during sample drying is small due to a full (i.e., close to 180 degrees) surface tension angle between the sample and the hydrophobic surface;

FIG. 3A is a schematic illustration according to one embodiment of the present invention showing a system for cleanup of biological samples from contaminants prior to spectroscopy analysis;

FIG. 3B is a flowchart illustrating one method of the present invention;

FIGS. 4A-4C are schematic illustrations depicting matrix assisted laser desorption/ionization mass spectra of an ovalbumin sample;

FIGS. 5A-5C are schematic illustrations depicting matrix assisted laser desorption/ionization mass spectra of a sample containing a MS2 bacteriophage coat protein;

FIGS. 6A-6B are schematic illustrations depicting matrix assisted laser desorption/ionization mass spectra of a sample containing *B. globigii* spores.

DETAILED DESCRIPTION OF THE INVENTION

Referring now to the drawings, wherein like reference numerals designate identical, or corresponding parts throughout the several views, and more particularly to FIG. 1, FIG. 1 is a schematic illustration according to one embodiment of the present invention showing an increased area during sample drying for binding sample biomolecules to a target plate for spectroscopic analysis. A liquid sample deposited on the nominally hydrophobic sample plate of a MALDI apparatus spreads on the surface to a given surface tension angle. Liquid from the sample can then evaporate from the deposited liquid sample. FIG. 2 is a schematic illustration of a conventional technique showing that the binding area during sample drying is small due to a full (i.e., close to 180 degree) surface tension angle between the sample and the hydrophobic surface.

In one embodiment of the present invention, by decreasing the surface tension angle, a larger binding area is available resulting in an increased binding capacity. Binding in one embodiment of the present invention can be facilitated by non-specific binding of the sample to the surface of the support, which as noted above is usually in a hydrophobic state. The present invention in one embodiment addresses non-specific binding where specific binding species such as antibody binding to specific antigens are not necessarily employed. A smaller surface tension angle in this embodiment is achieved by adding a reagent/wetting agent to the sample or by choosing a surface with smaller hydrophobicity. For example, in one embodiment of the present invention, a C4 surface modification (or compound) or even a gold surface can be used instead of the conventional C18 surface. C4 designates a linear hydrocarbon compound with 4 carbon atoms in the chain whereas C18 is a longer hydrocarbon molecule with 18 carbon atoms in the chain.

Under controlled wetting conditions, proteins and peptides in the sample bind on the target plate to the hydrophobic groups present on the probe surface. Sample drying can be enhanced by both drying at elevated temperature conditions (e.g., above room temperature), and the addition of a wetting agent to the sample. Sample drying improves the interactions between for example C18 groups on the target plate surface and the protein molecules in the applied sample droplet, resulting in enhanced protein binding, which would otherwise be limited by diffusion rates. If the samples are not dried, the protein molecules on top portion of the solution may not be able to bind to the C18-surface because the diffusion from the top to the surface takes several hours. As a result, only the protein molecules that were present at the bottom of the sample droplet will be able to interact with C18 chain on the surface and bind to C18-surface in a short time. In one embodiment of the present invention, sample drying is within 2 min for sample temperatures between 40-60° C., whereas conventional room temperature drying would take about ten minutes.

Furthermore, controlling the wetting conditions between the liquid sample and the hydrophobic surface of the probe by using volatile additives/solvents can result in a "large" wetting area and as a consequence can result in an increased binding capacity of the probe. Large area as used herein is a relative term. In the absence of a wetting agent, the sample drop (aqueous solution) will appear as a sphere on the hydrophobic surface as illustrated in FIG. 2. This allows only a smaller area of the surface that is in contact with the sample and therefore binding will occur only in that smaller surface area. Once that smaller area is saturated with protein, then rest of the protein samples will remain on top without binding and will be removed during the washing step. On the other hand, when a wetting agent is added, the sample will not be a sphere anymore, and there will be more surface area in contact with the sample (as illustrated in FIG. 1). This will result in more protein molecules binding to the target plate surface. In one embodiment of the present invention, the use of wetting agents (as discussed above) decreases the surface tension angle resulting in effective binding of the peptides and proteins of interest. After drying, in one embodiment of the present invention, the biomolecules can be bound to a large area of the hydrophobic probe (e.g., 0.04-0.2 cm$^2$/sample spot with a typical MALDI target plate having several of such sample spots).

Accordingly, the present invention addresses the binding capacity of a support holding a liquid sample by an on-probe clean-up system and method affecting sample wetting to the support surface. In one embodiment of the present invention, methods have been developed to extract the protein directly onto a hydrophobic target plate where for example digesting medium such as enzymes can be used to digest the extracted protein. The sample can then be purified for example by simply washing out the contaminants and other interfering materials.

The binding of the biomolecules permits analytes even from complex mixtures of interfering materials such as environmental and biological clutters to be processed and detected. In one embodiment of the present invention, proteins from microorganisms including toxins are detectable. In one embodiment of the present invention, even samples having biological clutter including for example growth medium, salts, buffers, lipids, oligonucleotides, and detergents can be processed and detected.

Figure 3A:
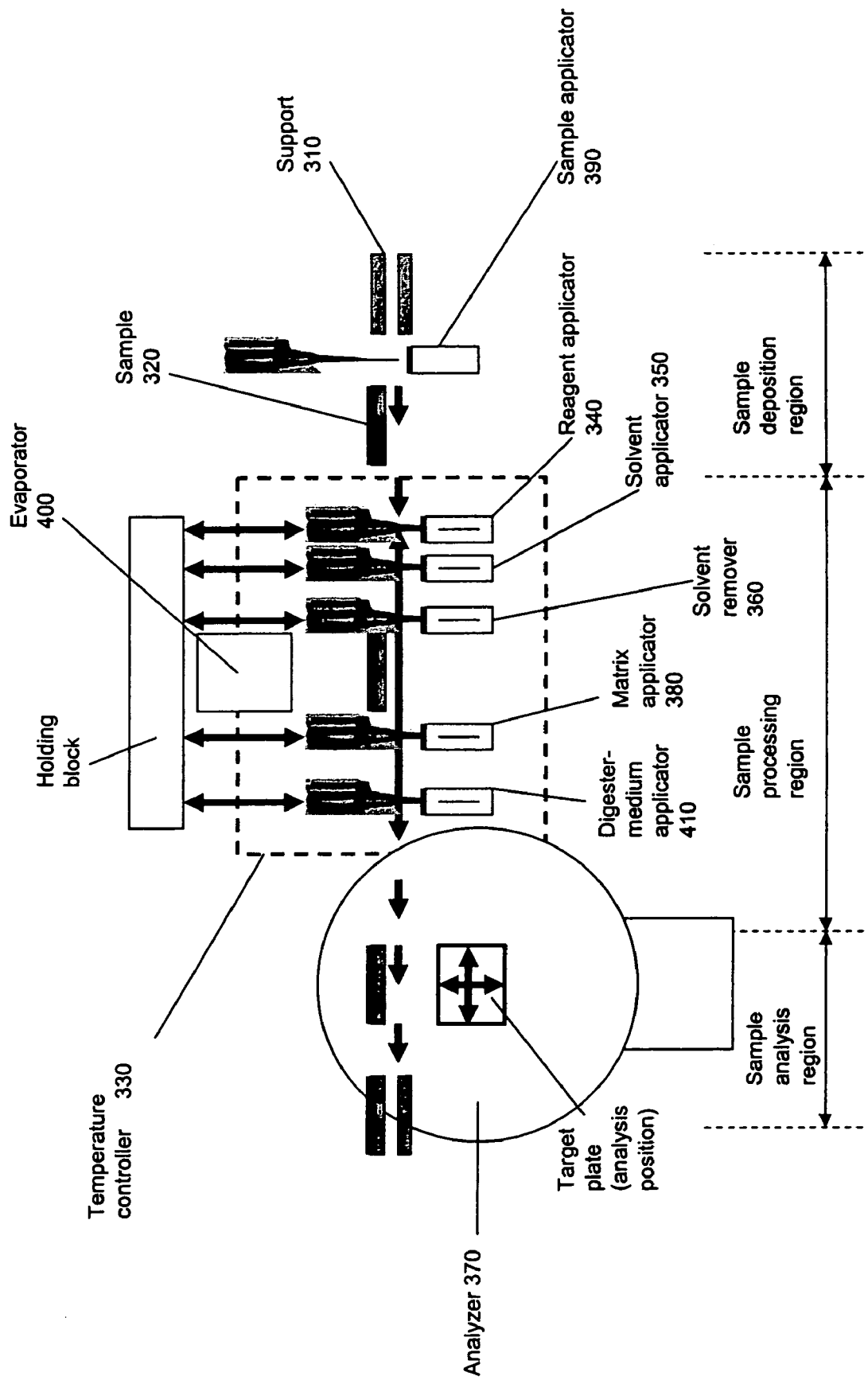

Referring now to FIG. 3A, which is a schematic illustration of one embodiment of the present invention showing a system for cleanup of biological samples from contaminants prior to spectroscopy analysis, the system 300 includes a support 310 that holds a sample 320 (i.e., at least initially a liquid sample) on the surface of the support to thereby control the surface tension of the liquid sample 320 in contact with the surface of support 310, as shown in FIG. 1. The liquid sample 320 can contain at least one group of biological molecules. The support 310 as shown in FIG. 3A has a surface that can nonspecifically bind the molecules thereon to the support (i.e., the surface can bind any hydrophobic molecule (biological or non-biological) that interacts with the C18 groups on the surface of the support.

In one embodiment of the present invention, the surface tension angle to the liquid is less than 180 degrees. In one embodiment of the present invention, the surface tension angle to the liquid is less than 160 degrees. In one embodiment of the present invention, the surface tension angle to the liquid is in a range from 70 to 160 degrees. In one embodiment of the present invention, the surface tension angle to the liquid is less than 140 degrees. In one embodiment of the present invention, the surface tension angle to the liquid is less than 120 degrees. In one embodiment of the present invention, the surface tension angle to the liquid is less than 90 degrees.

In one embodiment of the present invention, the support 310 can constitute a hydrophobic surface, a C18 phase surface, a C8 phase surface, a C4 phase surface, a gold surface, a stainless steel surface, a bare metal surface, a polymer surface, and combinations thereof. The support 310 in one embodiment can be a MALDI support and/or a MALDI target plate.

FIG. 3A shows schematically a time-wise progression of the support 310 holding the sample 320 from the depicted sample deposition region to the depicted sample processing region and then to the depicted sample analysis region. The system 300 as shown in FIG. 3A includes a temperature controller 330 for controlling a temperature of the liquid sample 320 on the support 310. The temperature controller 330 can include in number of conventional heating units such as resistive heaters, convection heaters, radiation heaters, etc. operated for example in a closed loop feedback with a temperature sensing device such as for example a thermocouple, a thermometer, or a wire-resistance thermometer. The temperature controller 330 as shown in FIG. 3A encompasses the sample processing region depicted, but in other embodiments can control temperature in the depicted sample deposition region.

As shown in FIG. 3A, the system 300 includes a reagent applicator 340. Suitable reagent applicators can be manual or automated dispensers including for example a reagent pipettor or dispenser. The reagent applicator 340 can be configured (through conventional metering controls and feeds) to supply the reagent to the support 310. Suitable reagents include water, a volatile buffer like ammonium bicarbonate buffer, a non-volatile buffer such as tris-buffer, and phosphate buffered saline (PBS), organic solvents, ethanol, methanol, isopropanol, acetone, and/or acetonitrile. Other solvents can be used in the present invention.

In one embodiment of the present invention, the reagent applicator 340 can supply an amount (e.g., a predetermined amount) of the reagent to the liquid sample on the support 310 to thereby produce the desired surface tension. While the present invention is not limited to the following, typically the volume of these solvents is usually the same volume as the sample that is taken for analysis (i.e., 1:1 by volume). Accordingly, the reagent applicator 340 can supply an amount (e.g., a predetermined amount) of the reagent resulting in a surface tension angle less than 140 degrees, less than 120 degrees, or less than 90 degrees. While not a rigorous limit, if the resultant angle is less than 70 degrees, then the sample will spread over such an area that the density of the sample and the resultant signal intensity from the mass spectrometer will decrease.

The system 300 includes a solvent applicator 350 for application of a solvent for dissolution of the contaminants in the liquid sample once evaporated. The system 300 includes a solvent removal device 360 for removal of the applied solvent from the evaporated sample, thereby removing at least a part of the contaminants. In certain cases, greater than 95% of contamination can be removed. Examples of contaminants removed include buffer salts, detergents, components of media used for growing cells, environmental or dust particles present in the bioaerosol collection, while retaining concentrations of proteins, peptides, lipids and toxins extracted from microorganisms or cells for further analysis.

The system 300 also includes solvent removal device 360. The solvent removal device 360 can be programmed to wash the solvent from the support 310, rinse the support 310 using the solvent, blow the solvent from the support 310 using forced air. The solvent removal device 360 can pipet the solvent from the support 310.

The system 300 as shown in FIG. 3A can include an analyzer 370. The analyzer 370 can be any one of a number of mass spectrometers including for example a tandem mass spectrometer or an ion mobility spectrometer. Such mass spectrometers can in one embodiment of the present invention be a matrix assisted laser desorption ionization (MALDI) mass spectrometer, a MALDI tandem mass spectrometer, an atmospheric pressure MALDI (AP-MALDI) mass spectrometer, or an AP-MALDI tandem mass spectrometer. The MALDI mass spectrometer can include a UV laser, an IR laser, a nitrogen laser, and a solid state laser or combinations of these and other suitable lasers for depositing energy into the matrix material. The analyzer 370 can be a MALDI ion mobility spectrometer. As illustrated in FIG. 3A, the sample in entering the sample analysis region can be rotated on a target plate for example of one of the MALDI mass spectrometers into a position for mass sampling, and then can be rotated back once complete.

The system 300 as shown in FIG. 3A can include a matrix applicator 380 for application of MALDI matrix material to the sample. Such matrix materials can include α-cyano-4-hydroxycinnamic acid, 2,5-dihydroxybenzoic acid, sinapinic acid, and ferulic acid. Other matrix materials specific to a laser source for the MALDI system in use can be applied to the sample in the present invention. Suitable matrix applicators can be manual or automated dispensers including for example pipettors (manual or automated) and automated liquid dispensers. The matrix applicator can be configured (through conventional metering controls and feeds) to supply the matrix to the support 310.

The system 300 as shown in FIG. 3A can include a sample applicator 390 for application of a liquid sample to the support 310. In one embodiment of the present invention, the sample applicator 390 can apply one of a protein sample, a peptide sample, an oligosaccharide sample, a DNA sample, a RNA sample, a lipid sample, and/or a phospholipids sample to the support 310. Suitable sample applicators can be manual or automated dispensers including for example pipettor or automated sample dispensing units. The sample applicator can be configured (through conventional metering controls and feeds) to supply the liquid sample to the support 310.

The system 300 as shown in FIG. 3A can include an evaporator 400 separate or as a part of the temperature controller 330. The evaporator 400 is designed to evaporate liquid from the liquid sample, and can be one of a forced gas evaporator, a forced air evaporator, a reduced pressure evaporator, or a heated evaporator. While the present invention is not limited to the following, a suitable temperature range of operation used for evaporation is 30° C. to 70° C., with the range of 40-60° C. typically used.

The system 300 as shown in FIG. 3A can include a digester-medium-applicator 410 for application of a digesting medium to the support 310. The digester medium is capable of digestion of biological molecules on the support 310. Suitable digester-medium-applicators can be manual or automated dispensers including for example pipettor and automated liquid dispensing system. Suitable digesting medium include trypsin, chymotrypsin, glycosidase and other enzymes (soluble or immobilized) In one embodiment of the present invention, the application of trypsin, chymotrypsin, glycosidase, and other enzymes is in the form of immobilized on beads or agarose. The above mentioned enzymes can be immobilized (covalently bound to) on crosslinked 4% beaded agarose gel support or immobilized on POROS 20 μm beads (both of which are commercially available).

The liquid sample 320 may include at least one of a salt, a buffer, a PBS buffer, a culture media component (ingredient), a cell debri, a microbial cell debri, cell wall components, cell membrane components, a detergent, and sodium dodecyl sulfate. These materials are considered as contamination that can be removed by the application of solvents for dissolution at least one of the salt, the buffer, the PBS buffer, the culture media, the cell debri, the microbial cell debri, the cell wall components, the cell membrane components, the detergent, and sodium dodecyl sulfate. These contaminations can be removed by selectively dissolving in water or volatile buffer such as ammonium bicarbonate buffer or less than 10% of organic solvents in water or the aqueous volatile buffer. The contaminants can then be removed from the probe surface using for example a pipettor.

Figure 3B:
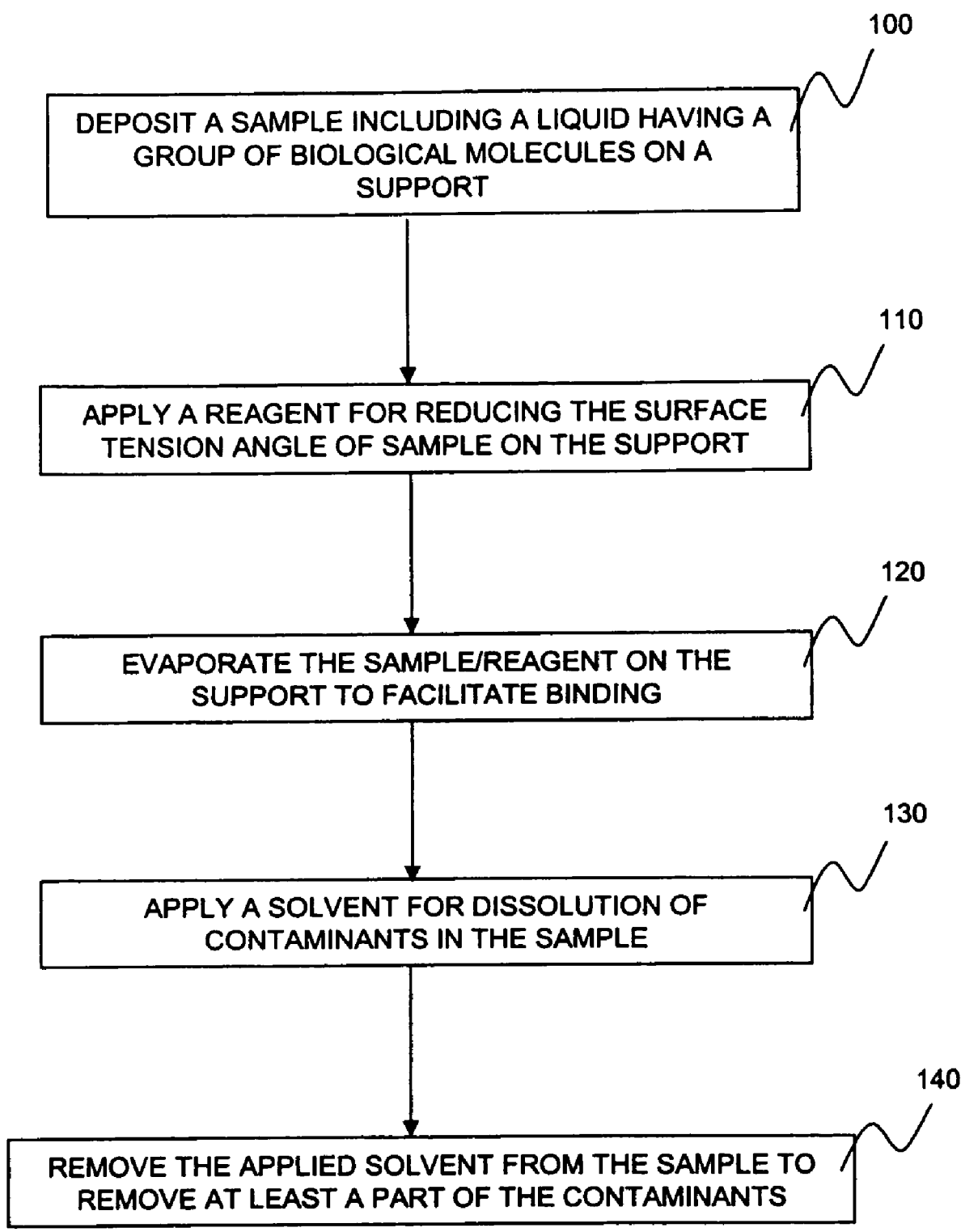

Referring now to one method embodiment of the present invention, FIG. 3B is a flowchart illustrating one method of the present invention for cleanup of biological samples from contaminants prior to spectroscopy analysis. At 100, a sample including a liquid having at least one group of biological molecules is deposited on a support. At 110, a reagent (e.g., a wetting agent) is added to reduce the surface tension angle of the liquid to the support to less than 180 degrees. At 120, the sample is then dried on the surface of the support by evaporation. At 130, a solvent for dissolution of the contaminants in the sample is applied. At 140, the applied solvent is removed from the sample to thereby remove at least a part of the contaminants.

At 100, for sample processing, a variety of samples can be deposited including a biological agent containing a microorganism, a spore, a cell culture, or a biological sample containing a protein, a peptide, an oligosaccharide, a DNA, a RNA, a lipid, a phospholipids, a toxin, or a combination thereof. Optimal binding of these biological molecules on the hydrophobic surface of the support can be achieved at a surface tension angle to the liquid sample of less than 160 degrees, less than 140 degrees, less than 120 degrees, less than 90 degrees, and/or in general in a range from 70 to 160 degrees.

As noted earlier, the surface tension angle can be a result of the hydrophobicity of the surface of the support to the biological sample or a result of solvent addition to the sample, or a combination thereof. Suitable reagents for sample processing during the process at 110 for control of the surface tension angle are those given above including water, a volatile buffer, ammonium bicarbonate, a non-volatile buffer, tris-buffer, an acid, trifluoroacetic acid, a base, ammonium hydroxide, an organic solvent, ethanol, methanol, isopropanol, acetone, acetonitrile, or a combination thereof.

Suitable solvents for the process at 130 for dissolution of the contaminants include water, a volatile buffer, ammonium bicarbonate, an organic solvent, ethanol, methanol, isopropanol, acetone, acetonitrile, or a combination thereof.

In one embodiment of the present invention, the sample temperature is controlled during the processing (for example by the temperature controller 330) Temperature control can assist in the evaporation of liquid or reagent from the sample. In one embodiment of the present invention, during processing, a matrix is added to the sample for assistance in laser desorption ionization of the sample. Suitable matrices for sample processing are those given above including α-cyano-4-hydroxycinnamic acid, 2,5-dihydroxybenzoic acid, sinapinic acid, and ferulic acid or a combination thereof.

In one embodiment of the present invention, during processing, a digesting medium is added to the sample. The digesting medium is capable of digestion of the biomolecules in the sample. Suitable digesting medium for sample processing are those given above including trypsin, chymotrypsin, glycosidase, other enzymes, or combinations thereof.

In one embodiment of the present invention, the sample after being deposited is allowed to dry, for example at an elevated temperature (e.g., above 30° C. and below 70° C., so as to evaporate faster without damaging the sample). Other temperatures are possible provided the temperatures do not themselves induce a change in the sample identity.

In one embodiment of the present invention, proteins bound to the surface can then be digested for example using enzymes such as the above noted enzymes immobilized trypsin. Digestion yields peptide fragments. Some of these peptide fragments (molecular weights ranging from 500 to 4000) assist in obtaining amino acid sequence information and hence form the basis as biomarkers.

The selective dissolution and removal of the contaminants in one embodiment of the present invention can be done after performing for example a tryptic digestion of the proteins, usually, by trypsin molecules immobilized to surface of small beads. As mentioned earlier, immobilized enzymes are commercially available. The above mentioned enzymes are immobilized (i.e., covalently bound to) on a cross-linked 4% beaded agarose gel support (Pierce Biotechnology, IL) or immobilized on POROS™ 20 μm beads (Applied Biosystems, CA). The present invention has found that the peptides generated by tryptic digestion will remain bound to the C18 groups on the probe surface after washing steps.

Similar to that discussed above, in one embodiment of the present invention, the presence of acetonitrile or other wetting additive in the trypsin mixture is beneficial for increasing the peptide binding area. In one embodiment of the present invention, dissolving and removing the contaminants will also remove the beads containing trypsin resulting in reduced trypsin autolysis peaks in the resultant mass spectrum. In one embodiment of the present invention, the addition of acetonitrile after adding trypsin enhances the area of binding of peptides to the hydrophobic surface and the activity of the trypsin A factor of 10 in terms of increased signal intensity has been observed with this procedure. Alternatively, as discussed below, the acetonitrile can be added before the trypsin, thereby enhancing the area of binding of protein to the hydrophobic surface. In this case, washing can also be performed before trypsin addition.

PREPARATION PROCEDURES AND EXAMPLES

Molecular Biology Grade water was purchased from Biowittaker (Walkersville, Md., USA). α-cyano-4-hydroxycinnamic acid (CHCA) was obtained from Fluka (Buch, Switzerland). A MALDI matrix solution was prepared as 10 mg/mL solution of CHCA in 60% acetonitrile/0.1% TFA. All other chemicals were purchased from Sigma Chemical Company (St. Louis, Mo., USA) and used without any further purification.

Immobilized trypsin beads (Poroszyme Bulk Immobilized Trypsin) were purchased from Applied Biosystems (Foster City, Calif., USA). Mass spectral experiments were carried out on a Thermo Finnigan (San Jose, Calif., USA) LCQ Deca XP ion trap mass spectrometer integrated with an AP/MALDI ion source (MassTech Inc., Columbia, Md., USA). A Thermo Laser Science Inc. (Franklin, Mass., USA) Model 337 Si nitrogen UV laser was used (λ=337 nm). Laser pulse duration was about 4 ns, and the laser beam was focused to approximately 500 μm size spot. The LCQ Deca XP ion trap mass spectrometer was operated in high mass range mode (up to 4000 Da), and was tuned and calibrated using the AP/MALDI source and standard proteins.

A hydrophobic target plate was prepared according to the following procedures. In brief, a MALDI target plate (in this example gold coated) was first cleaned by immersing in a solution of methanol/hydrochloric acid (1:1) for 30 minutes, followed by thoroughly rinsing with deionized water. The cleaned target plate was then dried completely and incubated in a 2 mM solution of octadecanethiol in absolute ethanol, overnight at room temperature. The target plate was then washed with fresh ethanol to remove any residual octadecanethiol. The target plate incubated in octadecanethiol results in a C18 surface.

*Escherichia coli* bacteriophage (MS2) was purchased from ATCC (Manassas, Va.) along with the host *Escherichia coli* strain C3000. MS2 bacteriophage was propagated and purified according to the previously published procedure. Spores of *Bacillus globigii* were obtained from the US government for analysis.

In one example of one embodiment of the present invention, a sample containing the proteins/peptides of interest was spotted on the target plate (typically 1 μL) and allowed to dry on the probe surface. Tryptic digestion of the protein was then carried out in-situ by adding trypsin immobilized on beads (typically 1 μL). Immediately after adding trypsin, an equal volume of acetonitrile was added (resulting in the 50% concentration of acetonitrile but concentrations in the range of 20-80% are also acceptable) to enhance the tryptic digestion and to increase the binding area of the peptides to the hydrophobic surface. Digestion was carried out until the spot dried.

Salts and other contaminating materials contained in original sample solution were then removed by washing with 3 μL of water (Scheme I shown below). 1 μL of matrix solution (10 mg/mL of CHCA in 70% acetonitrile in 0.1% trifluoro acetic acid)) was then added and dried.

Scheme I

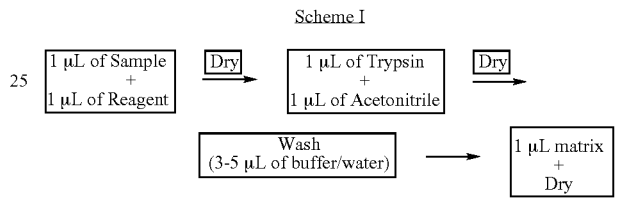

In another example of one embodiment of the present invention, contaminants and interfering materials were removed before the tryptic digestion of the proteins/peptides of interest (Scheme II shown below).

Scheme II

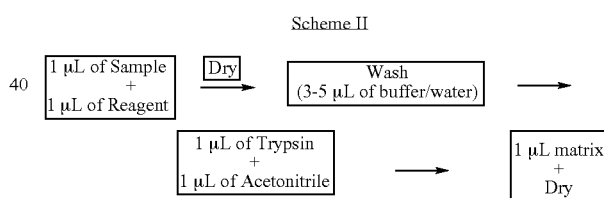

In this example, the sample was spotted on the target plate and allowed to dry on the probe surface. To increase wetting conditions (i.e., to decrease the surface tension angle), an additive changing the surface tension (a so-called wetting additive) was added to the sample before drying (usually acetonitrile or other reagents like trifluoroacetic acid TFA or ammonium hydroxide) to make the final concentration of the additive in the sample in the 20-80% range (typically 50%). Alternatively, 1 μL of acetonitrile (or other wetting reagent) can be added to the dried sample to enhance the interaction between C18 chain on the probe and the proteins/peptides in the sample.

After evaporation of the acetonitrile, salts and contaminants were removed by washing with 3 μL of water. Tryptic digestion of the protein bound to probe surface was then carried out by adding trypsin immobilized on beads (typically 1 μL) followed immediately by adding an equal volume of acetonitrile to enhance digestion. Digestion was carried out until the spot dried out. 1 μL of matrix solution (10 mg/mL of CHCA in 70% acetonitrile in 0.1% trifluoro acetic acid)) was then added and dried.

Detection of Ovalbumin:

When ovalbumin was dissolved in Phosphate Buffered Saline (PBS) buffer, MALDI mass spectral data was very difficult to obtain because of the interference from the buffer salts. In one embodiment of the present invention, removal of salts provided a suitable spectrum. The on probe clean up method of the present invention using the C18 hydrophobic target plate effectively removed the interfering salts and improved the quality of the spectrum for ovalbumin, as is evident by the increase in signal intensity and the absence of sodium adducts.

Figure 4A:
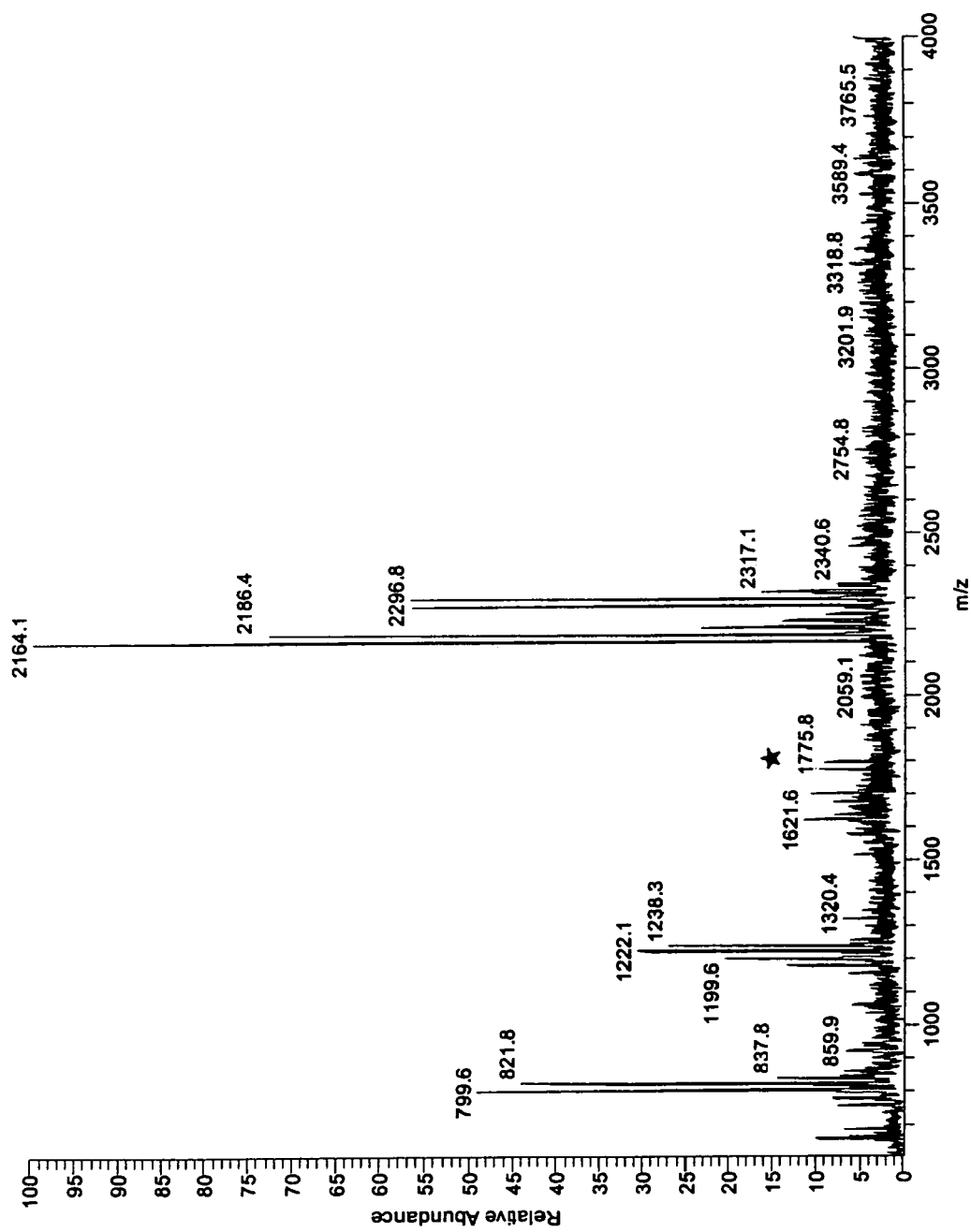
Figure 4B:
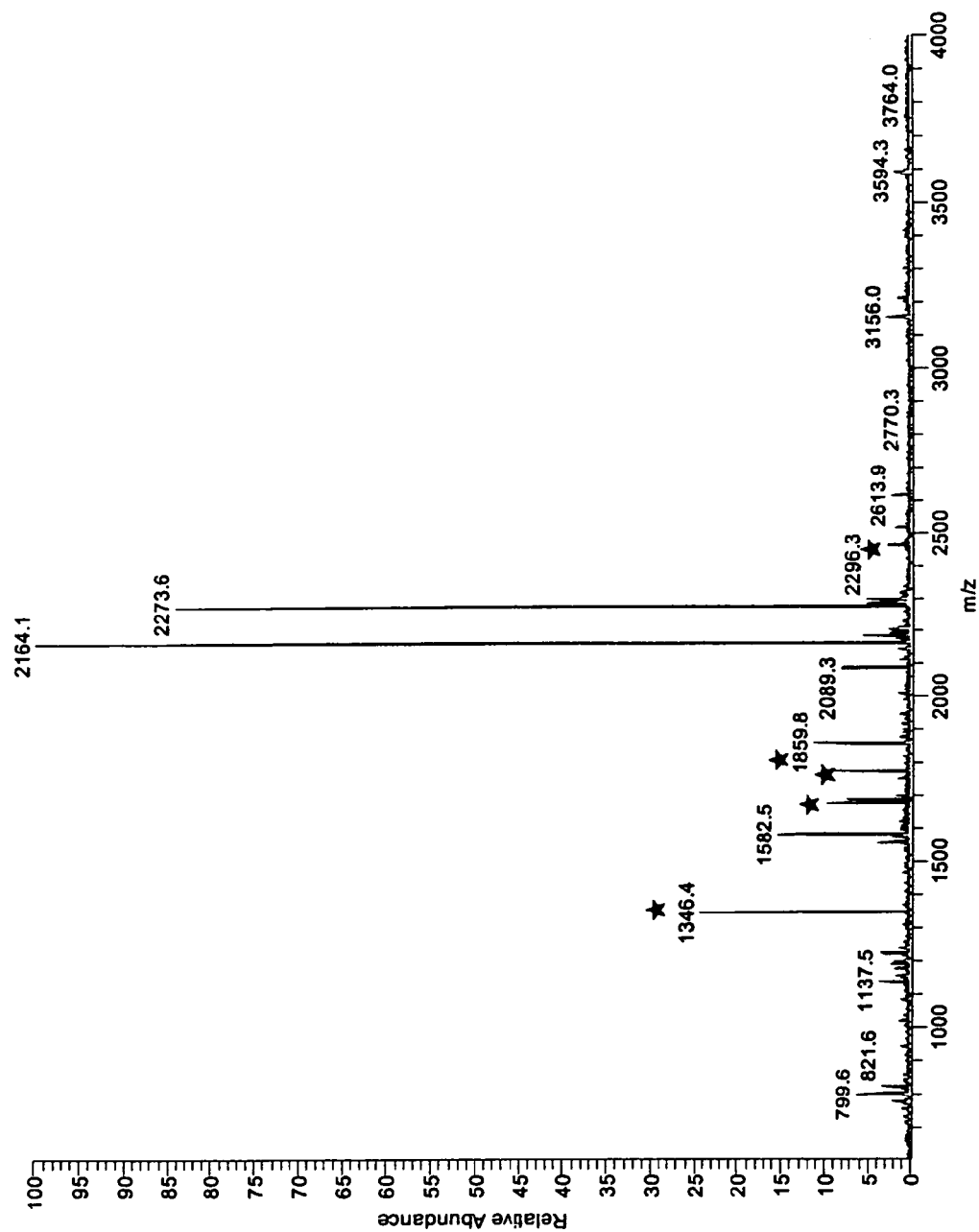
Figure 4C:
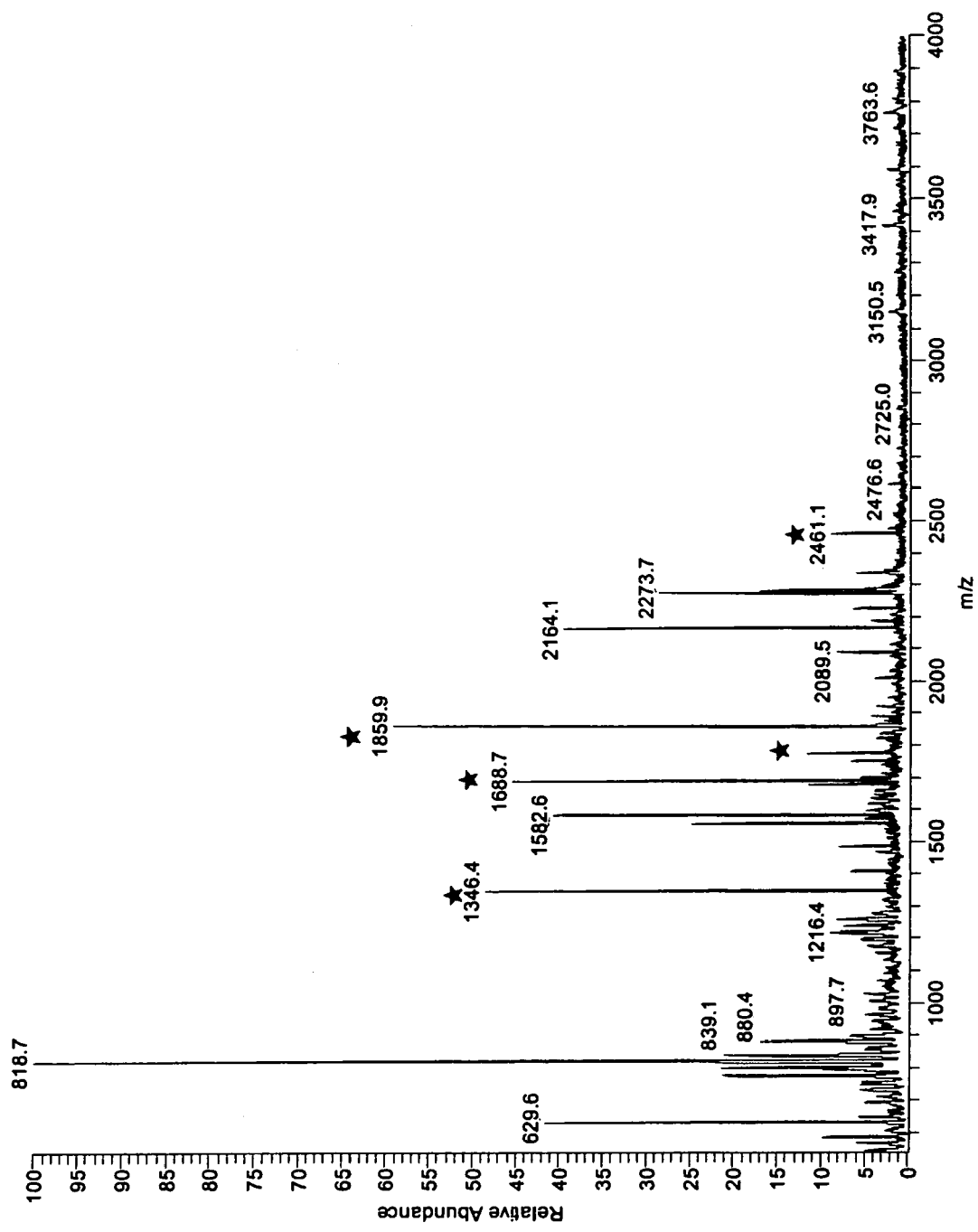

In this example of the present invention, ovalbumin in PBS was added to the target plate coated with C18 group and allowed to dry. Trypsin immobilized on beads was then added. Equal volume of acetonitrile was then added to enhance digestion and increase the peptide binding area. Digestion was allowed to occur until the solution dried. Addition of 3 µL of water to the dried spot followed by removal of the water using a pipette resulted in selectively dissolving the buffer salts and removing them from the probe surface leaving behind peptide fragments bound to the C18 groups on the probe surface as noted by the absence of sodium adducts in the spectrum (compare FIG. 4B to FIG. 4A). FIGS. 4A-4C are schematic illustrations depicting matrix assisted laser desorption/ionization mass spectra of ovalbumin in PBS after digestion with trypsin, without any clean up (FIG. 4A), after clean up with water on C18-target plate (FIG. 4B), and after clean up with water on bare gold target plate (FIG. 4C).

In one embodiment of the present invention, a similar clean-up effect was observed when a bare gold surface was used instead of the C18-modified surface (see FIG. 4C), although the hydrophobicity of the gold surface is much smaller compared to the C18 surface.

Detection of MS2 Bacteriophage

In another example of one embodiment of the present invention, a capsid protein of the MS2 bacteriophage was extracted and bound to the C18-probe or bare gold surface and digested using immobilized trypsin. The on probe clean up protocol was then used to remove debris from the viral sample (i.e., bioclutter), and the mass spectrum was recorded. MS2 bacteriophage sample with bioclutter was placed on the target plate followed by an equal volume of 50% ammonium hydroxide and the resulting solution was allowed to dry on the C18 probe surface. 1 µL of immobilized trypsin beads was then added to the dried out spot, followed immediately by 1 µL of acetonitrile (i.e., a wetting additive accelerating at the same time the digestion process), and the digestion was allowed until the spot dried.

The trypsin-digested sample mixture was cleaned by washing with 3 µL of water. The sample can also be cleaned up before the trypsin digest step. In this example, ammonium hydroxide worked as the wetting additive and at the same time as the capsid protein extraction reagent. 1 µL of matrix was then added on top of the digested and washed spot. This peptide-matrix mixture was allowed to dry and crystallize before recording the mass spectrum.

Figure 5A:
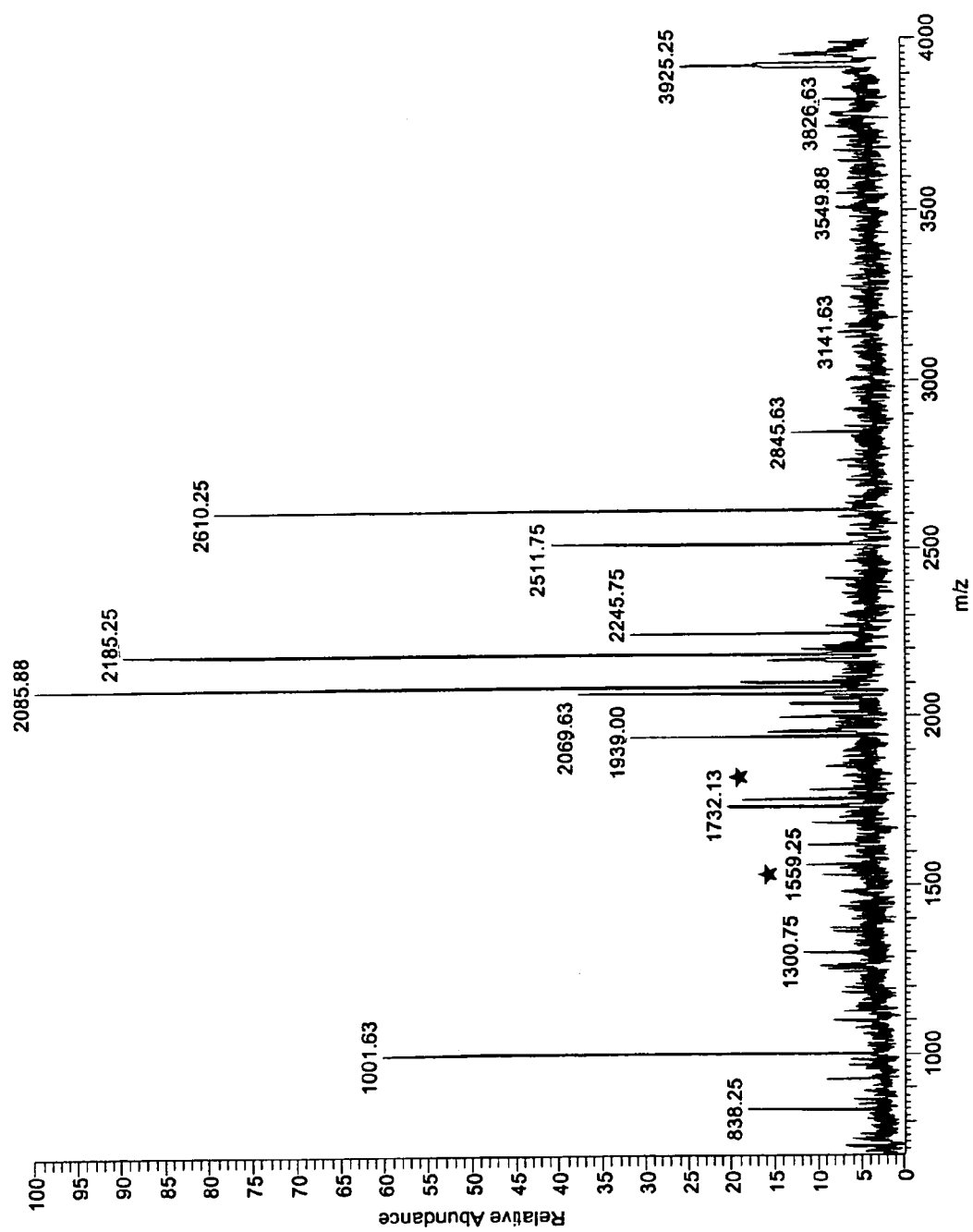
Figure 5B:
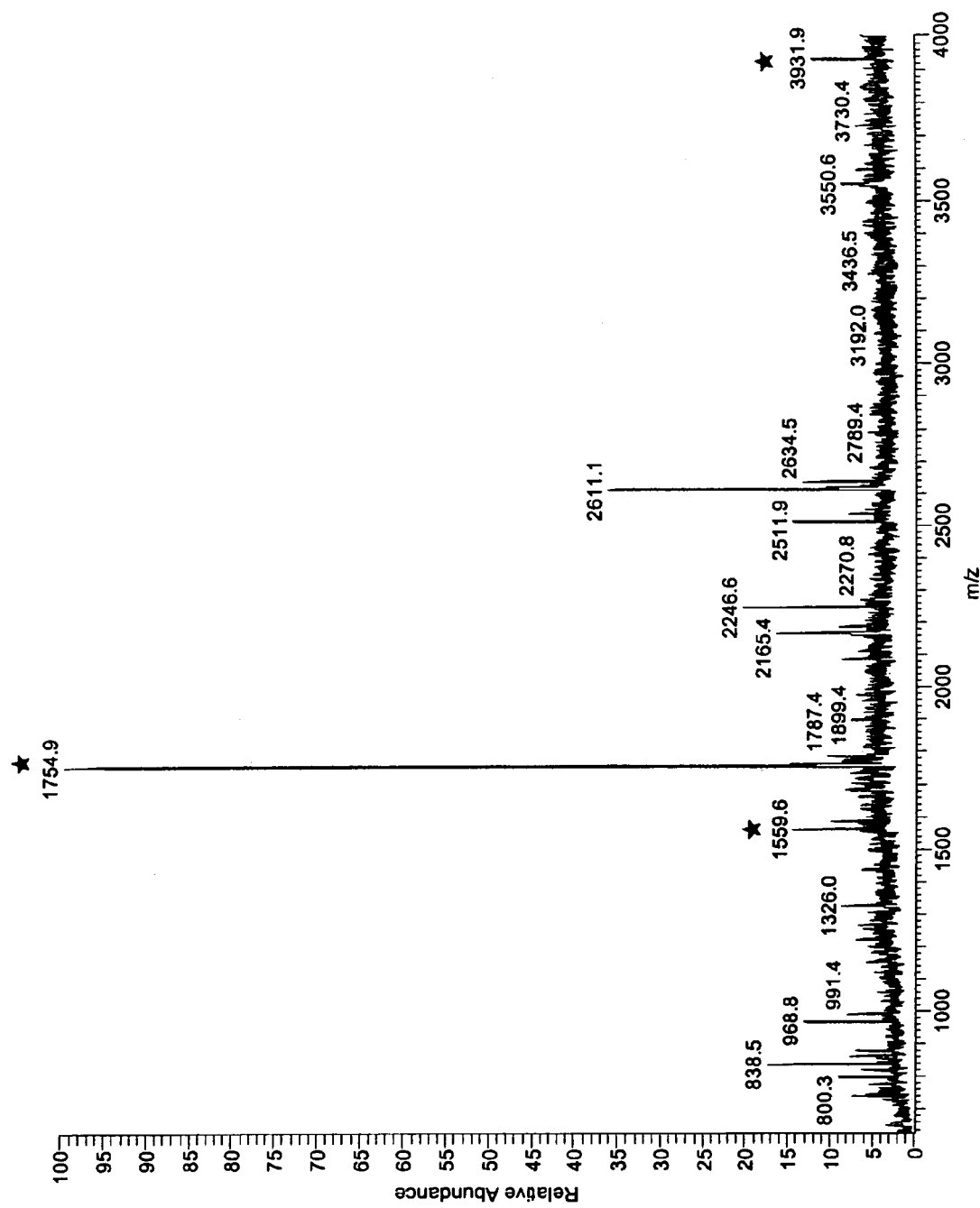
Figure 5C:
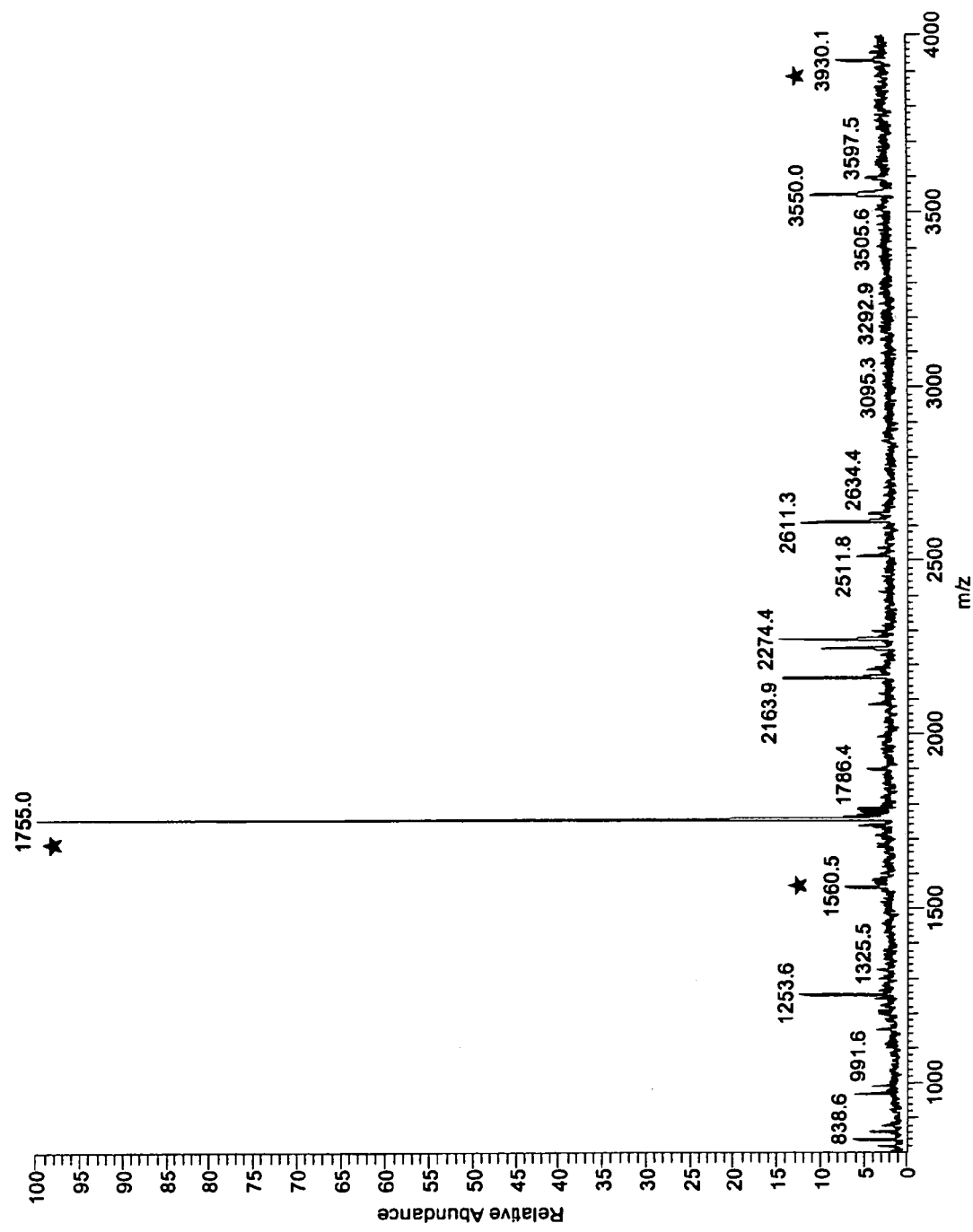

FIGS. 5A-5C are schematic illustrations depicting matrix assisted laser desorption/ionization mass spectra of a sample containing a MS2 bacteriophage coat protein after on probe extraction and trypsin digestion (without any clean up FIG. 5A), and after on probe clean up on C18-coated MALDI target plate before and after tryptic digestion of the extracted proteins (respectively in FIGS. 5B and 5C). FIGS. 5A-5C show the progression of mass spectra recorded. FIG. 5A is the spectrum obtained without any clean up. FIGS. 5B and 5C were obtained after on probe clean up on a C18-coated MALDI target plate before and after tryptic digestion of the extracted proteins.

Detection of Spores of *Bacillus globigii*

In another example of one embodiment of the present invention, small acid soluble proteins (SASP) from *B. globigii* spores were extracted and bound directly on to the C18-probe surface and digested using immobilized trypsin. The on probe clean up protocol of the present invention was used to remove rest of the spore materials, and the mass spectrum was recorded. 1 µL of the spore sample was placed on the target plate followed by 1 µL of 10% TFA which was used for the extraction of SASP from the spores, and the resulting solution was allowed to dry on the C18 probe surface. 1 µL of immobilized trypsin beads was then added to the dried spot, followed immediately by 1 µL of acetonitrile to increase the wetting and binding area and the digestion was allowed to occur until the spot dried out.

Trypsin digested sample mixture was cleaned by washing with 3 µL of water (add 3 µL of water and remove it using pipette). 1 µL of matrix was then added on top of the washed spot. This peptide-matrix mixture was allowed to dry and crystallize before recording the mass spectrum.

Figure 6A:
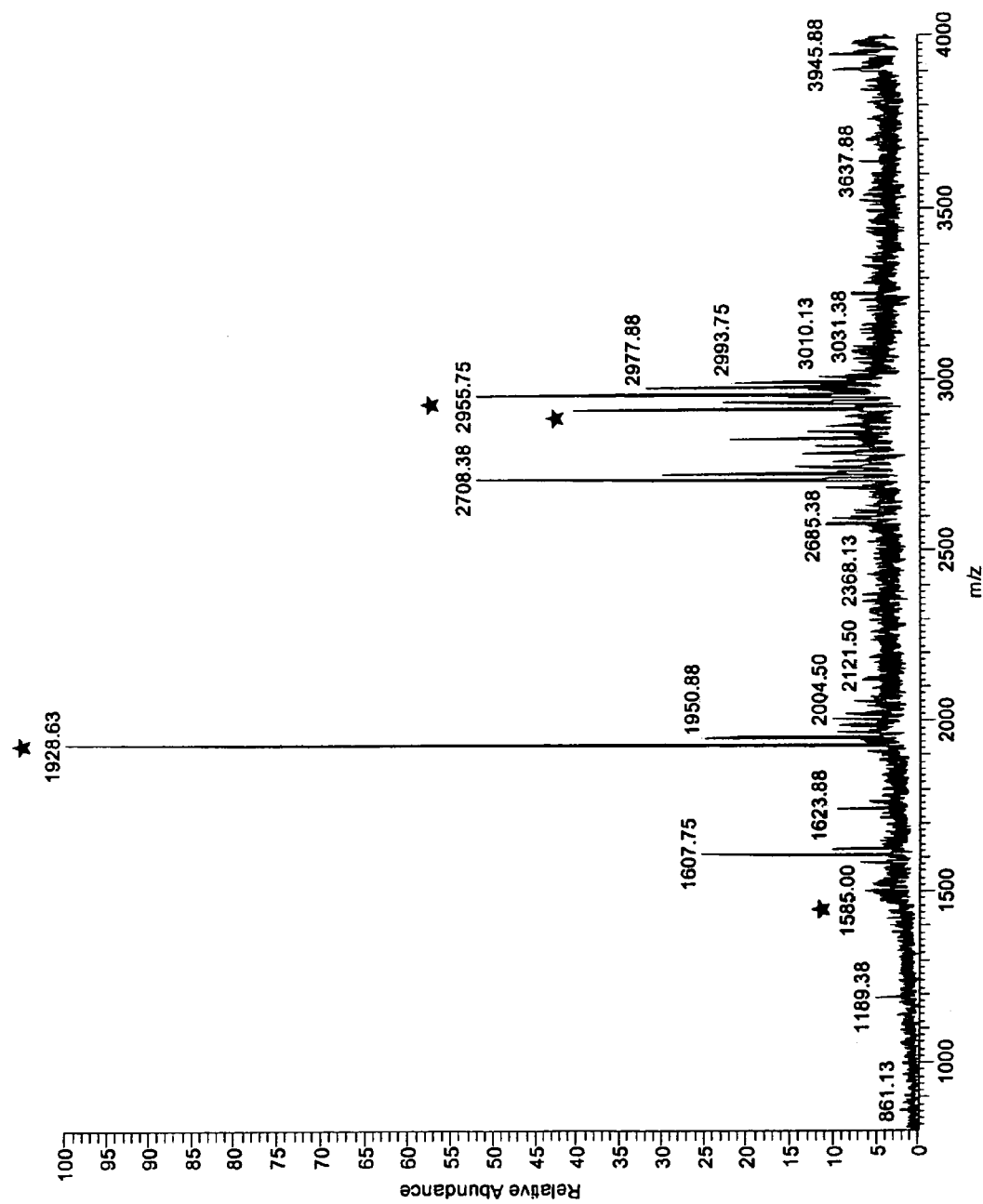
Figure 6B:

FIGS. 6A-6B are schematic illustrations depicting matrix assisted laser desorption/ionization mass spectra of a sample containing *B. globigii* spores after on probe extraction and trypsin digestion, without any clean up (in FIG. 6A), and after on probe clean up on C18-MALDI plate (in FIG. 6B). FIGS. 6A and 6B illustrate the effectiveness of the on probe cleaning method of the present invention for detecting the spores of *B. globigii*. FIG. 6A shows the mass spectrum without any clean up while FIG. 6B shows the spectrum after on probe clean up on C18-MALDI plate after the extraction and digestion of SASPs. While not shown, in one embodiment of the present invention, the cleanup step can also be done after the SASP extraction step. In this case TFA was used as the extraction reagent and at the same time as the wetting additive to increase the protein binding area.

Numerous modifications and variations on the present invention are possible in light of the above teachings. It is, therefore, to be understood that within the scope of the accompanying claims, the invention may be practiced otherwise than as specifically described herein.

The invention claimed is:

1. A system for cleanup of biological samples from contaminants prior to spectroscopy analysis, comprising:
    a support configured to hold a sample including a liquid having at least one group of biological molecules, a surface of the support binding the molecules to the support;
    a reagent applicator configured to apply to the support a reagent for reducing a surface tension angle between the liquid and a surface of the support to less than 180 degrees;
    an evaporator configured to evaporate liquid from the support;
    a solvent applicator configured to apply to the support a solvent for dissolution of the contaminants in the sample; and
    a solvent removal device configured to remove the applied solvent from the sample and thereby remove at least a part of the contaminants.

2. The system as in claim 1, further comprising:
    an analyzer for analysis of the sample, including at least one of a mass spectrometer, a tandem mass spectrometer or an ion mobility spectrometer.

3. The system as in claim 2, wherein the mass spectrometer comprises:
at least one of a MALDI mass spectrometer, a MALDI tandem mass spectrometer, an AP-MALDI mass spectrometer, or an AP-MALDI tandem mass spectrometer.

4. The system as in claim 3, wherein the mass spectrometer includes at least one of a UV laser, an IR laser, a nitrogen laser, a solid state laser, or a combination of thereof.

5. The system as in claim 3, further comprising:
a matrix applicator configured to apply a matrix to the sample for assistance in laser desorption ionization of the sample.

6. The system as in claim 5, wherein the matrix includes at least one of α-cyano-4-hydroxycinnamic acid, 2,5-dihydroxybenzoic acid, sinapinic acid, and ferulic acid or a combination thereof.

7. The system as in claim 1, further comprising:
a sample applicator configured to apply to the support at least one of a microorganism, a spore, or a cell culture, or a biomolecule including a protein, a peptide, an oligosaccharide, a DNA, a RNA, a lipid, a phospholipids a toxin, or a combination thereof.

8. The system as in claim 1, wherein the reagent applicator is configured to apply to the support at least one of water, a volatile buffer, ammonium bicarbonate, a non-volatile buffer, tris-buffer, an acid, trifluoroacetic acid, a base, ammonium hydroxide and tris-carbonate, an organic solvent, ethanol, methanol, isopropanol, acetone, acetonitrile, or a combination thereof.

9. The system as in claim 1, wherein the reagent applicator is configured to apply to the support an amount of the reagent such that the surface tension angle produced is less than 160 degrees.

10. The system as in claim 9, wherein the reagent applicator is configured to apply the support an amount of the reagent such that the surface tension angle produced is in a range from 70 to 160 degrees.

11. The system as in claim 1, wherein the surface of the support is configured to produce a surface tension angle of less than 160 degrees.

12. The system as in claim 9, wherein the surface of the support is configured to produce a surface tension angle in a range from 70 to 160 degrees.

13. The system as in claim 1, wherein the support comprises:
at least one of a hydrophobic surface, a polytetrafluoroethane surface, a C18 surface, a C8 surface, a C4 surface, a gold surface, a silver surface, a stainless steel surface, a metal surface, and a polymer surface.

14. The system as in claim 1, wherein the support is configured to non-specifically bind the biological molecules to the surface of the support.

15. The system as in claim 1, wherein the support comprises:
at least one of a MALDI support and a MALDI target plate.

16. The system as in claim 1, wherein the evaporator is configured to evaporate the liquid from the support by utilizing one of natural evaporation, forced gas evaporation, forced air evaporation, evaporation at reduced pressure, and evaporation at elevated temperatures.

17. The system as in claim 1, wherein applying a solvent comprises:
applying to the sample at least one of water, a volatile buffer, ammonium bicarbonate, trifluoroacetic acid, an organic solvent, ethanol, methanol, isopropanol, acetone, acetonitrile, or a combination thereof.

18. The system as in claim 1, wherein the solvent removal device is configured to at least one of wash the sample with the solvent, blow the solvent from the sample, or collect the solvent in a pipet.

19. The system as in claim 1, further comprising:
a digester-medium applicator configured to apply to the sample a digesting medium capable of digestion of the biomolecules in the sample.

20. The system as in claim 19, wherein the digester-medium applicator is configured to apply to the sample enzymes including at least one of trypsin, chymotrypsin, glycosidase, or combinations thereof.

21. A method for cleanup of biological samples from contaminants prior to spectroscopy analysis, comprising:
depositing on a support a sample including a liquid having at least one group of biological molecules,
adding a reagent agent to the deposited sample to reduce the surface tension angle between the liquid and a surface of the support to less than 180 degrees;
drying the sample by evaporation;
applying to the sample a solvent for dissolution of the contaminants in the sample; and
removing the applied solvent from the sample to thereby remove at least a part of the contaminants.

22. The method as in claim 21, wherein the depositing comprises:
binding the biological molecules on the surface of the support at a surface tension angle to the liquid sample of less than 160 degrees.

23. The method as in claim 21, wherein the depositing comprises:
binding the biological molecules on the surface of the support at a surface tension angle to the liquid sample in a range from 70 to 160 degrees.

24. The method as in claim 21, further comprising:
evaporating the sample on the support by utilizing at least one of natural evaporation, forced gas evaporation, forced air evaporation, evaporation at reduced pressure, or evaporation at elevated temperatures.

25. The method as in claim 21, further comprising:
applying a matrix to the sample for assistance in laser desorption ionization of the sample.

26. The method as in claim 25, wherein the applying comprises:
applying at least one of α-cyano-4-hydroxycinnamic acid, 2,5-dihydroxybenzoic acid, sinapinic acid, and ferulic acid or a combination thereof.

27. The method as in claim 21, wherein the depositing comprises:
depositing for the sample at least one of a microorganism, a spore or a cell culture, or a biomolecule including a protein, a peptide, an oligosaccharide, a DNA, a RNA, a lipid, a phospholipids a toxin, or a combination thereof.

28. The method as in claim 21, wherein applying a reagent comprises:
applying to the sample at least one of water, a volatile buffer, ammonium bicarbonate, a non-volatile buffer, tris-buffer, phosphate buffered saline, an acid, trifluoroacetic acid, a base, ammonium hydroxide and tris-carbonate, an organic solvent, ethanol, methanol, isopropanol, acetone, acetonitrile, or a combination thereof.

29. The method as in claim 21, wherein the applying a reagent comprises:
applying an amount of the reagent such that the surface tension angle produced is less than 160 degrees.

30. The method as in claim 21, wherein the applying a reagent comprises:

applying an amount of the reagent such that the surface tension angle produced is in a range from 70 to 160 degrees.

31. The method as in claim 21, wherein the depositing comprises:
non-specifically binding the biological molecules to a surface of the support.

32. The method as in claim 21, further comprising:
applying to the sample a digesting medium capable of digestion of the biomolecules in the sample.

33. The method as in claim 32, wherein the applying a digesting medium comprises:
applying to the sample at least one of trypsin, chymotrypsin, glycosidase, other enzymes, or combinations thereof.

34. The method as in claim 32, wherein the applying a digesting medium is performed before or after removing contaminants.

35. The method as in claim 21, wherein applying a solvent comprises:
applying to the dried sample at least one of water, a volatile buffer, ammonium bicarbonate, trifluoroacetic acid, an organic solvent, ethanol, methanol, isopropanol, acetone, acetonitrile, or a combination thereof.

36. The method as in claim 21, wherein the removing the solvent comprises at least one of:
washing the sample with the solvent, blowing the solvent from the sample, and collecting the solvent in a pipet.

37. The method as in claim 21, wherein the contaminants include at least one of buffer salts, PBS buffer, culture media, cell debris, detergents, or sodium dodecyl sulfate.

38. The method as in claim 21 where the reagent reducing the surface tension angle can be added directly to the sample before depositing on the support.

39. A system for cleanup of biological samples from contaminants prior to spectroscopy analysis, comprising:
a support configured to hold a sample including a liquid having at least one group of biological molecules, a surface of the support binding the molecules to the support;
a reagent applicator configured to apply to the support a reagent for reducing a surface tension angle between the liquid and a surface of the support to less than 180 degrees;
a solvent applicator configured to apply to the support a solvent for dissolution of the contaminants in the sample; and
a solvent removal device configured to remove the applied solvent from the sample and thereby remove at least a part of the contaminants.

40. A method for cleanup of biological samples from contaminants prior to spectroscopy analysis, comprising:
depositing on a support a sample including a liquid having at least one group of biological molecules,
adding a reagent to the deposited sample to reduce the surface tension angle between the liquid and a surface of the support to less than 180 degrees;
applying to the sample a solvent for dissolution of the contaminants in the sample; and
removing the applied solvent from the sample to thereby remove at least a part of the contaminants.

* * * * *